United States Patent [19]

Pennington

[11] Patent Number: 4,959,486
[45] Date of Patent: * Sep. 25, 1990

[54] ALKYLENE OXIDES PRODUCTION FROM ALKANES OR ALKYLAROMATICS USING MOLTEN NITRATE SALT CATALYST

[75] Inventor: B. Timothy Pennington, Sulphur, La.

[73] Assignee: Olin Corporation, Cheshire, Conn.

[*] Notice: The portion of the term of this patent subsequent to Nov. 15, 2005 has been disclaimed.

[21] Appl. No.: 402,091

[22] Filed: Aug. 3, 1989

Related U.S. Application Data

[60] Division of Ser. No. 238,714, Aug. 31, 1988, Pat. No. 4,885,374, and a continuation-in-part of Ser. No. 929,552, Nov. 12, 1986, Pat. No. 4,785,123.

[51] Int. Cl.$^5$ ............................................ C07D 301/06
[52] U.S. Cl. ...................................... 549/532; 549/533
[58] Field of Search ........................ 549/518, 532, 533

[56] References Cited

U.S. PATENT DOCUMENTS

| | | | |
|---|---|---|---|
| 2,366,724 | 1/1945 | Gardner | 549/533 |
| 2,530,509 | 11/1950 | Cook | 260/348.5 |
| 3,132,156 | 5/1964 | Lemon et al. | 260/348 |
| 3,641,157 | 2/1972 | Riegel et al. | 260/599 |
| 3,647,358 | 3/1972 | Greenberg | 549/533 |
| 3,786,109 | 1/1974 | Jones | 260/673 |
| 3,850,742 | 11/1974 | Dugan et al. | 260/683 R |
| 4,785,123 | 11/1988 | Pennington | 549/532 |

FOREIGN PATENT DOCUMENTS

| | | |
|---|---|---|
| 968364 | 5/1975 | Canada . |
| 0268870 | 6/1988 | European Pat. Off. . |

Primary Examiner—Robert T. Bond
Assistant Examiner—Ba K. Trinh
Attorney, Agent, or Firm—Dale Lynn Carlson

[57] ABSTRACT

A process for producing an alkylene oxide or mixture of alkylene oxides by a reaction which comprises reacting an alkane or alkylaromatic compound mixture thereof with an oxygen-containing gas in the presence of at least one molten nitrate salt catalyst.

10 Claims, No Drawings

ALKYLENE OXIDES PRODUCTION FROM ALKANES OR ALKYLAROMATICS USING MOLTEN NITRATE SALT CATALYST

This application is a division of Ser. No. 238,714, filed 8/31/88, now U.S. Pat. No. 4,885,374, and a continuation-in-part application of U.S. Pat. application Ser. No. 929,552, filed Nov. 12, 1986, now U.S. Pat. No. 4,785,123.

BACKGROUND OF THE INVENTION

Alkylene oxides (vicinal epoxy alkanes), and particularly propylene oxide, are very valuable and widely used chemicals. They have been polymerized with a wide variety of monomers to yield polymers which are useful in coating compositions and in the manufacture of molded articles. Alkylene oxides have also been reacted with alcohols to yield monoalkyl ethers which have utility as solvents in many commercial processes and which are useful as components for synthetic turboprop and turbojet lubricants.

There are many methods known in the art for the production of alkylene oxides and, most notably, propylene oxide. One of the oldest methods is the so-called "chlorohydrin process" which involves the reaction of chlorine and water to form hypochlorous acid which is then reacted with propylene to form propylene chlorohydrin. The propylene chlorohydrin is then dehydrohalogenated to yield propylene oxide. Another method to obtain propylene oxide is by the liquid phase oxidation of propylene with organic peracids Still another method involves the liquid phase oxidation of propylene with t-butyl hydroperoxide and/or ethylbenzene hydroperoxide.

The aforementioned known methods have serious disadvantages associated therewith. For example, the "chlorohydrin process" requires the use of chlorine which is relatively expensive and corrosive in nature, requiring special handling and expensive equipment. Additionally, the chlorohydrin saponification to propylene oxide consumes alkali chemicals such as caustic soda or lime, producing a large aqueous waste stream containing chloride salts, which require costly treatment prior to discharge from the plant. The oxidation of propylene with peracids is a potentially dangerous operation and expensive equipment is needed to guard against potentially explosive hazards when working with the peracids. Another disadvantage of this method is the high cost of peracids. The t-butyl hydroperoxide and ethylbenzene hydroperoxide processes have the disadvantages of being capital-intensive, multi-step, rather complicated processes. Furthermore, these processes require co-feedstocks of isobutane or ethylbenzene, thus constraining the practical utility of the processes for propylene oxide manufacture.

Another method which has received considerable attention in the literature is the direct oxidation of hydrocarbons with an oxygen-containing gas. This method suffers from the disadvantage that it is not specific for the production of alkylene oxides but produces a variety of other compounds including acids, esters, ethers, and oxides of carbon including carbon monoxide and carbon dioxide. The reaction does, however, possess two attributes which recommend it highly for commercial utilization, i.e., inexpensiveness of starting materials and simplicity of operation. It is primarily for these reasons that much attention in recent years has been directed to improvements in methods for the production of alkylene oxides from the direct oxidation of hydrocarbons even though the producer must necessarily contend with the concurrent production of a variety of undesired products.

By way of illustration, the prior art methods which attempted to produce propylene oxide by the oxidation of propane such as that disclosed in U.S. Pat. No. 2,530,509, assigned to Linde Air Products Company, were only partially successful. The majority of the prior art methods used conventional vertical columns and differed from each other by variations in lengths and diameter of the column, temperature, pressure, etc. However, all of these methods suffered one common disadvantage—the temperature of the reactants varied throughout the length of the column.

The temperature variations are easily explained since the oxidation reactions are exothermic and the amount of heat evolved differs with each reaction which is taking place. Thus, at various increments along the tube, conditions existed which favored the direction of the oxidation to products other than propylene oxide. These prior art methods necessitated the use of elaborate and expensive cooling apparatus.

Further developments in the art constituted attempts to maximize the desired olefin oxide production while minimizing by-product formation. For example, U.S. Pat. No. 3,132,156, assigned to Union Carbide Corporation, discloses the vapor phase oxidation of saturated aliphatic hydrocarbons to olefin oxides. The method described in this '156 patent is said to provide enhanced olefin oxide production as high as 46.2 lbs per 100 lbs of $C_3$ consumed which calculates to be about 33 percent (molar) selectivity. While this level of selectivity constituted an improvement, it remains less than might be desired from a commercial standpoint. Likewise, Canadian Patent 968,364, assigned to Union Carbide Corporation, discloses the indirect oxidation of olefin oxides via the oxidation of methanol to a free radical intermediate which in turn, epoxidizes the olefin. However, the indirect oxidation method disclosed in the Canadian '364 patent has the disadvantage of requiring the use of a solvent together with subsequent solvent separation step(s). Accordingly, new methods of producing olefin oxides that combine enhanced selectivity with a simple, inexpensive process would be highly desirable.

SUMMARY OF THE INVENTION

The present invention relates to a process for producing an alkylene oxide or mixture of alkylene oxides by a reaction which comprises reacting an alkane or alkylaromatic compound having from 3 to 22 carbon atoms per molecule, or mixture thereof, with an oxygen-containing gas, said alkane or alkylaromatic compound and said oxygen-containing gas being gaseous reactants, by contacting said gaseous reactants with a bath, stream, spray or mist of at least one molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres.

DETAILED DESCRIPTION OF INVENTION

Several factors will affect the reactant conversion to alkylene oxide and the selectivity of alkylene oxide production vis-a-vis by-product production in accordance with the process of the present invention. These factors include, for example: the contact time of the molten salt with the oxygen-containing gas, the temperature of the reactor product gases, the molten salt temperature, the molten salt catalyst composition, the feed gas temperature, the feed gas composition, the feed gas pressure, and the co-catalyst employed.

The oxygen-containing gas useful as a reactant in the present invention can be any such gas. Typically, air is employed as the oxygen-containing gas based upon its ready availability. However, other oxygen-containing gases such as pure oxygen may be employed if desired, and the use of oxygen is expected to be preferred in a commercial setting.

The alkane useful in the present invention can be broadly defined as saturated hydrocarbon compound having from 3 to 22 carbon atoms, preferably from 3 to 15 carbon atoms, more preferably from 3 to 12 carbon atoms, most preferably from 3 to 8 carbon atoms. Typical alkanes include propane, butane, isobutane, pentane, hexane, octane, and dodecane. Especially advantageous alkanes are those having 3 to 6 carbon atoms When a straight-chain alkane is employed, it is more preferred that such molecule not have more than eight carbon atoms. When a cyclic alkane is used, it is more preferred that such molecule not have more than 12 carbon atoms per molecule. A particularly preferred reactant within this group is propane or a mixture of propane and propylene based upon its commercial availability.

The alkane gas is preferably preheated to prevent condensation in the line delivering this gas to the reactor. Alternatively, both the oxygen-containing gas and the alkane gas (collectively referred to herein as "the feed gases") can be preheated to prevent condensation in any of the feed lines. However, in the absence of preheat, the molten nitrate salt will rapidly heat the feed gases up to reaction temperature. If the feed gas is preheated, it preferably is maintained at at least about 100° C. in the feed gas line(s).

The molten nitrate salt(s) catalyst is generally maintained at a temperature sufficient to keep the salt(s) in a molten condition. Preferably, the temperature is maintained between about 135° C. (275° F.) and about 600° C. (1,000° F.), more preferably between about 200° C. and about 600° C., most preferably between about 250° C. and about 550° C. during the reaction in accordance with the present invention.

The specific temperature selected is based upon the melting point of the particular molten nitrate salt chosen. For example, mixtures of molten lithium and potassium nitrate can be suitably employed at a temperature as low as about 280° F., and hence, this temperature may be employed when using lithium nitrate. In the selection of a suitable molten nitrate salt bath temperature, it is important to choose a temperature below the thermal decomposition temperature for the particular molten nitrate salt chosen. In addition, it is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" oxidation reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The nitrate salt catalyst used may be any one of the alkali or alkaline earth nitrates such as lithium, sodium, potassium, rubidium, cesium, magnesium, calcium, strontium, or barium or mixtures thereof. In addition, the nitrate salts can be used in mixtures with other salts such as chlorides, bromides, carbonates, sulfates, and phosphates. Generally, the content of the other salt(s), when present, should be restricted to less than 60 percent by weight based upon the weight of the total melt and in most cases their contents should not exceed about 25 percent of the total melt.

The ratio of alkane to oxygen in the oxygen-containing gas in the reactor can vary over a wide range. However, in accordance with the present invention, it has now been found that enhanced selectivity of alkylene oxide product is achieved by maintaining a relatively low amount of oxygen relative to the amount of alkane fed into the reactor. For example, when reacting propane with oxygen in a molten potassium nitrate salt column at atmospheric pressure, a ratio of between about 1 and about 20 volume percent of oxygen, e.g., about 5 volume percent oxygen to about 95 volume percent propane is expected to provide an enhanced selectivity of propylene oxide. When using air as the oxygen-containing gas, it is preferably employed in an amount of between about 5 and about 75 volume percent based upon the total amount of air plus propane employed in the reaction. Another consideration in the selection of the amount of propane or other alkane to use as a feed is the high partial pressure of the alkane which in high concentrations can cause thermal cracking of the alkane reactant itself. Therefore, when conducting the oxidation reaction at an elevated pressure, viz 75 psig, it is preferred to "cut" the amount of propane in the illustrative example to 75 volume percent and utilize an inert blanket ("diluent") gas, such as nitrogen, to provide the remaining 20 volume percent of feed gas. Alternatively, the diluent gas may be comprised of mixtures of oxidation by-product gases such as acetaldehyde, methane, and carbon dioxide, generally readily obtainable from the propylene oxide purification operations downstream of the molten salt reactor.

In the selection of the ratio of the volume of oxygen-containing gas relative to the volume of alkane employed in the reaction mixture, the range of ratios which might pose a flammability hazard should be avoided, as is well known. For example, when utilizing an air/propane reactant mixture at atmospheric pressure, the range of below 10 volume percent of propane based upon total air plus propane should be avoided.

A co-catalyst can also be used in accordance with the present invention. It has been found that an elemental metal, or the oxide or hydroxide thereof, when employed as a co-catalyst in conjunction with the molten nitrate salt catalyst, makes it possible to lower the reaction temperature for the particular nitrate salt selected and/or enhance the selectivity or conversion to the desired olefin oxide. For example, it has been found in accordance with the present invention that although a temperature of about 380° C. is normally required when reacting propane with air to produce propylene oxide in the presence of sodium nitrate at atmospheric pressure, the temperature can be reduced to 350° C. provided that a co-catalyst of palladium on alumina is employed in conjunction with the molten salt. A silver co-catalyst such as silver nitrate, or a molybdenum oxide co-catalyst is expected to similarly reduce the required reaction temperatures. The use of these metal co-catalysts are preferred when the reaction is conducted at atmospheric pressure. At superatmospheric pressure, an alkali metal hydroxide co-catalyst, such as sodium hydroxide, has been found to be particularly advantageous in providing enhanced selectivity to the desired product. In addition, in a continuous process employing caustic recycle, the alkali metal hydroxide is expected to enhance the desired product distribution by removing by-product carbon dioxide by forming alkali metal carbonate.

The co-catalyst (if used) is generally employed in a catalytically effective amount, generally in an amount of less than about 5 (preferably between about 0.5 and about 5, more preferably in an amount between about 0.5 and about 3) weight percent based on the total amount of co-catalyst plus molten salt catalyst.

The molten salt catalyst in which the co-catalyst (if used) is suspended or dispersed, helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

Typically, the molten salt(s) is employed in an amount on a weight basis of between about 5 times and about 100 times (preferably between about 5 times and about 50 times) the total weight of the reactants employed.

The molten salt(s), in addition to functioning as a catalyst and as an isothermal medium for any co-catalyst, also serve as a temperature regulator. More specifically, the molten nitrate salt(s) have a high heat absorption capacity, enabling them to absorb large quantities of heat during the exothermic oxidation reaction while maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperature.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture. Another preferred molten mixture is a mixture of sodium, lithium and potassium nitrate salts, preferably in a ratio of between about 10 and about 30 weight percent of lithium nitrate and between about 15 and about 75 weight percent of sodium nitrate based on the total amount of the mixture.

One method of contacting the gaseous reactants in the presence of the molten nitrate salt is by bubbling the reactants through a bath of the molten salt. If the gaseous reactants are bubbled into the bottom of the bath or column containing the molten nitrate salt, the contact time of the reactants with the molten salt catalyst is equal to the "rise time" of the reactants through the bath or column. Thus, the contact time can be increased by increasing the length of the molten nitrate salt bath or column. An alternate method of contacting the gaseous reactants in the presence of the molten salt would be to pass the gaseous reactants through a reactor countercurrently to a spray or mist of the molten salt. This latter method provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gas-liquid contact in reaction systems may also be employed.

The alkane feed gas(es) can be passed into the molten nitrate salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially-mounted feed gas tubes are employed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

If a bath of molten salt is employed, the feed gas is preferably bubbled into the molten nitrate salt-containing reactor using a sparger. If used, the sparger is preferably positioned in the molten nitrate salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas in the other tube will maintain sufficient pressure to keep the molten salt from backing up into the unpressurized feed gas tube.

This process can be run in a batchwise or continuous operation, the latter being preferred. The order of introduction of the reactants is determined by the operator based on what is most safe and practical under prevalent conditions. Generally, the desirability of avoiding flammable gas mixtures throughout the reaction and subsequent product separation systems will dictate the desired procedures.

The process can be carried out by feeding a mixture of alkane, inert gas, and oxygen into a reaction vessel containing molten nitrate salt. The reaction vessel can be glass, glass-lined metal, or made of titanium. For example, a glass-lined stainless steel autoclave can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation helps prevent crust formation of the salt(s) at the head gas/salt interface in the reactor. This can be accomplished by using a mechanically stirred autoclave, a multi-point injection system, or a continuous process, e.g., with a loop reactor wherein the reactants are force circulated through the system. Sparging can also be used. In the subject process, it is found that increased rates of reaction are obtained by good gas-liquid contact provided by agitation of the molten salt/gas mixture.

The process of the present invention is suitably carried out at atmospheric, subatmospheric or superatmospheric pressure. Typically, the process is effected at superatmospheric pressures of up to about 100 atmospheres, preferably between about 1 atmosphere and about 50 atmospheres, more preferably between about 1 atmosphere and about 35 atmospheres. The most preferred pressure range is between about 1 and about 25 atmospheres.

It is to be understood that by-products are also produced during the reaction. For example, some fragmentation and dehydrogenation of the propane feed is also effected, particularly at higher temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation.

The following examples are intended to illustrate, but in not way limit the scope of, the present invention.

EXAMPLE 1

Atmospheric Pressure Reaction of Isobutane Preheated Before Entering the Reactor and Oxygen in a Molten Salt Mixture of 55% Sodium Nitrate and 45% Potassium Nitrate A six liter cylindrical stainless steel flanged-top reactor approximately 76 cm deep and 10 cm in diameter was filled with 5,500 g NaNO$_3$ and 4,500 g KNO$_3$. The salt mixture was melted and brought up to 454° C. by use of externally wrapped electrical resistance heating coils. Isobutane was preheated to 240° C. and then fed at the rate of 810 cc/min into the melt through a porous metal sparging element submerged at a depth of 51 cm in the molten salt. Oxygen at the flow rate of 220 cc/min was sparged into the melt through a ⅛ inch stainless steel line, the end of which was located directly beneath the isobutane sparger, so that the air and isobutane contacted each other After running the experiment for 45 minutes, the flows were stopped and the contents of the cold trap and gas sample bomb placed in the product stream lines were analyzed. The cold trap was found to contain 5.0 ml of condensate analyzed as 70 percent water, with the balance mainly methanol and 1,2-isobutylene glycol. The gas sample was found to contain 90 percent isobutane, 3.5 percent oxygen, 1.6 percent carbon dioxide, and the balance was various reaction products including isobutylene oxide, propane, and acetone as major products. The conversion of isobutane was calculated by gas chromatography to be 7.2 percent. The selectivities of various products were calculated and are given in Table I below.

TABLE I

| Compound | Molar Selectivity (%) |
|---|---|
| CO$_2$ | 12.2 |
| Isobutylene Oxide | 16.5 |
| Propylene | 4.4 |
| Isobutylene | 23.2 |
| Acetone | 14.2 |
| Methanol | 4.9 |
| 1,2-Isobutylene Glycol | 3.4 |
| Propylene Oxide | 3.5 |
| Ethylene | 0.5 |
| 2-Methylacrolein | 2.1 |
| Other | 15.2 |

EXAMPLE 2

Atmospheric Pressure Reaction of Propane With Oxygen in a Molten Salt Bath

A reaction was carried out as in EXAMPLE 1 except that propane was used instead of isobutane. The product distribution calculated from gas chromatography data is shown in TABLE II.

TABLE II

| Compound | Molar Selectivity (%) |
|---|---|
| Carbon Dioxide | 12.1 |
| Carbon Monoxide | 2.8 |
| Methanol | 21.6 |
| Formaldehyde | 6.4 |
| Ethylene | 9.3 |
| Propylene | 5.7 |
| Butenes | 2.1 |
| Acetaldehyde | 14.2 |
| Propylene Oxide | 13.1 |
| Acrolein | 4.4 |
| Acetone | 2.6 |
| Allyl Alcohol | 1.5 |
| Other | 4.2 |

EXAMPLE 3

Atmospheric Pressure Reaction of Ethylbenzene With Air in Molten Nitrate Salt

Ethylbenzene was injected into the gas inlet tube of the same reactor as described in EXAMPLE 1 at the rate of 0.15 cc/min. Air was sparged through the feed tube sweeping the ethylbenzene into the molten nitrate salt mixture. The flow rate of the air was about 1000 cc/min at just slightly greater than atmospheric pressure. The molten salt temperature was maintained near 450° C. The experiment was allowed to continue for 30 minutes and then stopped. The reactor exit condensate was collected in a dry ice-isopropanol trap. Reactor exit gas samples and condensate (2.61 grams) were analyzed by gas chromatography methods and by GC/MS. The ethylbenzene conversion was about 1 percent. The reaction products were styrene, styrene oxide, benzaldehyde, acetophenone, carbon monoxide, and carbon dioxide.

EXAMPLE 4 (PROPOSED EXAMPLE)

Atmospheric Pressure Reaction of Isooctane With Oxygen in a Molten Nitrate Salt Mixture The reaction of isooctane with oxygen is carried out in the same manner as in EXAMPLE 1, except that isooctane is used instead of isobutane and that the isooctane is fed into the molten salt reactor as a liquid instead of a gas. When such an experiment is performed, one of the major reaction products is found to be isooctene oxide (1,2-epoxy-2,4,4-trimethylpentane). Other products include methyl(2,2-dimethyl)-propyl ketone, carbon monoxide, and carbon dioxide.

EXAMPLE 5 (PROPOSED EXAMPLE)

Atmospheric Pressure Reaction of 2-Methylundecane With Oxygen in a Molten Nitrate Salt Mixture The reaction of 2-methylundecane with oxygen is carried out in the same manner as in the PROPOSED EXAMPLE 4, except that 2-methylundecane is used in place of isooctane. When such an experiment is performed, one of the major products is found to be 2-methyl-2,3-epoxyundecane. Other products include acetone, nonyl aldehyde, carbon monoxide, and carbon dioxide.

EXAMPLE 6

Higher Pressure Reaction of Isobutane With Oxygen in a Molten Nitrate Salt Mixture Isobutane vapor at the rate of 625 cc/min, oxygen at rate of 375 cc/min, and nitrogen at the rate of 1500 cc/min were sparged into a molten nitrate salt mixture as described in EXAMPLE 1. The reactor pressure was maintained at 75 psig and the molten salt temperature was held near 375° C. The reactant gases were fed into the reactor for one hour and then the reactant gas flows were shut off. Analysis of the reactor off gas samples and the condensate sample showed that 25.4 percent of the isobutane fed in had been reacted. The major products were isobutylene, acetone, isobutylene oxide, methanol, carbon monoxide, and carbon dioxide.

I claim:

1. A product for producing an alkylene oxide or mixture of alkylene oxides by a reaction which comprises reacting an alkane or alkylaromatic compound having from 3 to 22 carbon atoms per molecule, or mixture thereof, with an oxygen-containing gas, said alkane or alkylaromatic compound and said oxygen-containing gas being gaseous reactants, by contacting said gaseous reactants with a bath, stream, spray or mist of at least one molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres, said process additionally employing a co-catalyst selected from the group consisting of elemental metals, and oxides and hydroxides thereof, and mixtures thereof, said co-catalyst being suspended, dispersed or disolved in said molten nitrate salt catalyst.

2. A method for producing an alkylene oxide from an alkane or alkylaromatic compound having from 3 to 22 carbon atoms per molecule or mixture thereof, which comprises bubbling gaseous reactants consisting of an oxygen-containing gas and said alkane or alkylaromatic compound, or mixture thereof, through a bath of at least one molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres, said method additionally employing a co-catalyst selected from the group consisting of elemental metals, and oxides and hydroxides thereof, and mixtures thereof, said co-catalyst being suspended, dispersed or disolved in said molten nitrate salt catalyst.

3. A process for producing an alkylene oxide or mixture of alkylene oxides by a reaction which comprises reacting an alkane or alkylaromatic compound having from 3 to 8 carbon atoms per molecule, or mixture thereof, with an oxygen-containing gas, said alkane or alkylaromatic compound and said oxygen-containing gas being gaseous reactants, by contacting said gaseous reactants with a bath, stream, spray or mist of at least one molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres, said process additionally employing a co-catalyst selected from the group consisting of elemental metals, and oxides and hydroxides thereof, said co-catalyst being suspended, dispersed or dissolved in said molten nitrate salt catalyst.

4. The process of claim 1 wherein said co-catalyst is an alkali metal hydroxide.

5. The process of claim 4 wherein said alkali metal hydroxide is selected from the group consisting of sodium hydroxide, potassium hydroxide, and combinations thereof.

6. The process of claim 1 wherein said co-catalyst is palladium, silver or molybdenum oxide.

7. The process of claim 2 wherein said co-catalyst is an alkali metal hydroxide.

8. The process of claim 7 wherein said co-catalyst is selected from the group consisting of sodium hydroxide, potassium hydroxide, and combinations thereof.

9. The process of claim 3 wherein said co-catalyst is palladium, silver or molybdenum oxide.

10. The process of claim 3 wherein said co-catalyst is an alkali metal hydroxide.

* * * * *

UNITED STATES PATENT AND TRADEMARK OFFICE
CERTIFICATE OF CORRECTION

PATENT NO. : 4,959,486
DATED : September 25, 1990
INVENTOR(S) : Pennington

It is certified that error appears in the above—identified patent and that said Letters Patent is hereby corrected as shown below:

In column 9 at line 36 delete "product" and insert --process--.

Signed and Sealed this

Ninth Day of June, 1992

Attest:

DOUGLAS B. COMER

Attesting Officer      Acting Commissioner of Patents and Trademarks